United States Patent
Joost et al.

(10) Patent No.: US 9,320,844 B2
(45) Date of Patent: Apr. 26, 2016

(54) ARRANGEMENT FOR REMOVING CARBON DIOXIDE FROM AN EXTRACORPOREAL FLOW OF BLOOD BY MEANS OF INERT GASES

(75) Inventors: Thilo Joost, Friedberg (DE); Rainer Kobrich, Neulussheim (DE)

(73) Assignee: MAQUET VERTRIEB UND SERVICE DEUTSCHLAND GMBH, Rastatt (DE)

( * ) Notice: Subject to any disclaimer, the term of this patent is extended or adjusted under 35 U.S.C. 154(b) by 20 days.

(21) Appl. No.: 14/234,939
(22) PCT Filed: Jul. 27, 2012
(86) PCT No.: PCT/EP2012/064801
§ 371 (c)(1),
(2), (4) Date: Apr. 14, 2014
(87) PCT Pub. No.: WO2013/014276
PCT Pub. Date: Jan. 31, 2013

(65) Prior Publication Data
US 2014/0216252 A1     Aug. 7, 2014

(30) Foreign Application Priority Data
Jul. 27, 2011 (DE) .......................... 10 2011 052 187

(51) Int. Cl.
A61M 1/36 (2006.01)
A61M 1/16 (2006.01)
B01D 19/00 (2006.01)

(52) U.S. Cl.
CPC ........... *A61M 1/3633* (2013.01); *A61M 1/1698* (2013.01); *A61M 2202/025* (2013.01); *A61M 2202/0291* (2013.01); *B01D 19/0031* (2013.01)

(58) Field of Classification Search
CPC ............... B01D 19/0031; B01D 53/22; B01D 2257/504; A61M 1/1698; A61M 1/3627; A61M 1/3633; A61M 2202/025; A61M 2202/0291

USPC ............................................... 96/6; 95/46, 51
See application file for complete search history.

(56) References Cited

U.S. PATENT DOCUMENTS

| 5,225,161 A | 7/1993 | Mathewson et al. |
| 5,277,176 A * | 1/1994 | Habashi et al. .......... 128/200.24 |

(Continued)

FOREIGN PATENT DOCUMENTS

| CN | 1486197 A | 3/2004 |
| DE | 3142751 A1 | 6/1982 |

(Continued)

OTHER PUBLICATIONS

International Search Report for PCT/EP2012/064801 dated Nov. 28, 2012.
English Translation of Chinese Office Action U.S. Appl. No. 201280037664.4 dated Jun. 18, 2015.

*Primary Examiner* — Jason M Greene
(74) *Attorney, Agent, or Firm* — Westley Scott Ashton

(57) ABSTRACT

The invention relates to an arrangement (10, 100, 200) for removing carbon dioxide from an extracorporeal flow of blood. The arrangement (10, 100, 200) comprises a filter (12) which has a membrane (16) that separates a blood region (14) from a gas region (18). The extracorporeal flow of blood is passed through the blood region (14) of the filter (12). Likewise, a gas flow of a purge gas is passed through the gas region (18), the purge gas being an inert gas or a mixture of inert gases. Further, the invention relates to a method for removing carbon dioxide from an extracorporeal flow of blood in which likewise an inert gas or a mixture of inert gases is used as a purge gas.

9 Claims, 3 Drawing Sheets

(56) References Cited

U.S. PATENT DOCUMENTS

| | | | |
|---|---|---|---|
| 2004/0057869 A1* | 3/2004 | Dingley | 422/48 |
| 2006/0144235 A1* | 7/2006 | Clarke et al. | 96/5 |
| 2006/0231098 A1* | 10/2006 | Downie et al. | 128/204.22 |
| 2009/0081079 A1 | 3/2009 | Johns | |
| 2010/0143192 A1* | 6/2010 | Myrick et al. | 422/45 |
| 2012/0129149 A1* | 5/2012 | Federspiel et al. | 435/2 |
| 2013/0068222 A1* | 3/2013 | Schmidt | 128/203.12 |

FOREIGN PATENT DOCUMENTS

| | | |
|---|---|---|
| DE | 231988 A5 | 1/1986 |
| DE | 60031706 T2 | 9/2007 |
| EP | 0183250 A2 | 11/1985 |
| WO | 0243792 A1 | 6/2002 |
| WO | 03092776 A2 | 11/2003 |
| WO | 2009004419 A1 | 1/2009 |

\* cited by examiner

ARRANGEMENT FOR REMOVING CARBON DIOXIDE FROM AN EXTRACORPOREAL FLOW OF BLOOD BY MEANS OF INERT GASES

CROSS REFERENCE TO RELATED APPLICATIONS

This application is entitled to the benefit of and incorporates by reference subject matter disclosed in International Patent Application No. PCT/EP2012/064801 filed on Jul. 27, 2012 and German Patent Application No. 10 2011 052 187.9 filed Jul. 27, 2011.

TECHNICAL FIELD

The invention relates to an arrangement for removing carbon dioxide from an extracorporeal flow of blood, the arrangement comprising a filter having a membrane that separates a blood region from a gas region. The extracorporeal flow of blood is passed through the blood region of the filter, and a gas flow of a purge gas is passed through the gas region of the filter.

BACKGROUND

In medicine, in the case of seriously ill patients so-called oxygenators are used to remove carbon dioxide from the blood of these patients and to oxygenate the blood. Nowadays, oxygenators comprising a membrane by which a blood region is separated from a gas region are used almost exclusively. The blood is taken from a main vessel of the patient and is fed into the blood region of the oxygenator preferably by means of a blood pump. At the same time, a purge gas is transported through the gas region, normally either pure oxygen or a mixture of oxygen and nitrogen being used as a purge gas. In particular, a mixture of 21% oxygen and 79% nitrogen, so-called AIR, is used. The purge gas is in particular taken from wall supplies available in medical facilities and thus meets the requirements of medical gases.

As a result of the pressure gradient of the partial pressure or the concentration gradient of the carbon dioxide, carbon dioxide is transported from the blood region through the membrane and into the gas region, whereas as a result of the partial pressure gradient of the partial pressure of the oxygen or the concentration gradient of the oxygen, the oxygen is transported through the membrane from the gas region into the blood region so that the blood is oxygenated while at the same time carbon dioxide is removed from the blood. The amount of carbon dioxide that is removed from the blood per unit of time, and the amount of oxygen with which the blood is oxygenated per unit of time depend, on the one hand, on the flow rate of the purge gas through the gas region and, on the other hand, on the transport rate of the blood through the blood region.

In known arrangements, the purge gas always comprises oxygen so that an oxygenation of the blood inevitably takes place even if the breathing capacity of the patient himself/herself were sufficient to ensure sufficient oxygen supply, and it were only necessary to remove the carbon dioxide from the blood. The unnecessary enrichment of the blood by means of the oxygenator can result in a hypoxic pulmonary vasoconstriction with a corresponding shunt shift so that the already ill patient is stressed further and his recovery is hindered. Depending on the purge gas used, moreover further gases may be transferred from the purge gas into the blood, which may also result in irritations of the patient.

SUMMARY

It is the object of the invention to specify an arrangement for removing carbon dioxide from an extracorporeal flow of blood, by means of which the carbon dioxide can be gently removed from the flow of blood.

This object is solved by an arrangement for removing carbon dioxide from an extracorporeal flow of blood, with a filter comprising a membrane that separates a blood region through which the extracorporeal flow of blood is passed from a gas region through which a gas flow of a purge gas is passed, wherein the purge gas is an inert gas or a mixture of inert gases. Advantageous developments of the invention are specified in the dependent claims.

According to the invention, this object is solved in that as a purge gas an inert gas or a mixture of inert gases is used. Thus, it is achieved that the purge gas does not enter into combination with the extracorporeal flow of blood so that no gases are supplied to the flow of blood but only carbon dioxide is removed from the extracorporeal flow of blood as a result of the partial pressure gradient or concentration gradient existing between the blood region and the gas region.

In this connection, a gas that does not enter into combination with blood is understood as an inert gas.

In case that only one inert gas is used as a purge gas, preferably nitrogen or a noble gas, in particular helium, neon, xenon, argon or krypton is used as an inert gas. When using a mixture of inert gases as a purge gas, a mixture of nitrogen and at least one noble gas or a mixture of at least two noble gases is used, accordingly.

As a filter, in particular an oxygenator is used so that carbon dioxide can be gently removed from the blood in an easy manner. Preferably, a blood pump is provided by means of which the flow of blood is transported through the blood region.

Further, a gas supply unit for generating a gas flow of the purge gas can be provided. The gas supply unit preferably comprises a gas blender by which the purge gas can be mixed from several inert gases. In addition, the gas supply unit can comprise a ventilator by means of which the gas flow of purge gas is generated. Alternatively, a gas supply unit can be dispensed with. In this case, the flow is generated by the pressure of the inert gas or the inert gases with which they are provided.

It is advantageous when at least one storage tank is provided, in which the purge gas is contained. The storage tank is connected to the filter via a supply line. Alternatively, also several storage tanks can be provided, wherein in this case a glas mixing unit, a so-called gas blender is provided, via which the gases contained in the storage tanks are mixed into the purge gas before the purge gas is then supplied to the supply line and, via this supply line, to the filter.

In a particularly preferred embodiment, a return line for returning the purge gas from the filter into the supply line is provided so that the purge gas can be used once again. Thus, the inert gases can be used several times, which, in particular when using noble gases as inert gases, results in a cost reduction.

In the area of the return line, in particular a cleaning unit for the at least partial removal of the carbon dioxide from the gas fed through the return line is provided. The cleaning unit removes in particular the entire carbon dioxide contained in the gas fed through the return line so that after passage through the cleaning unit the gas no longer contains any carbon dioxide and thus can be re-used for flowing through the gas region of the filter. The return line is in particular also connected to the gas blender so that via the gas blender the supplied gas can be mixed with the gas taken from the storage tank and thus the desired composition of the purge gas can be produced at any time.

For maintaining an adjustable flow rate in the return line, a gas transport unit is assigned to the system (preferably a turbine) is added. The transport capacity is subordinated to the adjustable gas flow through the filter and can be selected by the user.

Further, it is advantageous if a sensor for determining the carbon dioxide content of the purge gas is provided downstream of the filter. By means of this sensor it can in particular be monitored that the purge gas supplied to the filter does not contain any carbon dioxide so that the desired partial pressure gradient or concentration gradient of the carbon dioxide between the gas region and the blood region is established and the desired transfer capacity of carbon dioxide from the flow of blood into the purge gas is guaranteed.

Additionally or alternatively, a sensor for determining the carbon dioxide content of the purge gas can also be provided downstream of the filter so that by comparing the carbon dioxide content upstream and downstream of the filter, it can be determined how much carbon dioxide has been removed from the extracorporeal flow of blood via the filter. Thus, it can be monitored easily whether the desired preset transfer capacity of the carbon dioxide has actually been achieved. In particular, a monitoring of the condition of the patient is thus possible.

Further, it is advantageous if a respective sensor for determining the flow rate of the purge gas is provided downstream and/or upstream of the filter. Thus, the flow rate of the purge gas can easily be monitored, and in particular by comparing the determined flow rate or the determined flow rates to a preset desired value and a corresponding control of the flow rate it can be guaranteed that the preset flow rate is actually kept so that the desired preset transfer capacity is achieved.

Further, the arrangement comprises in particular a control unit which controls the gas supply unit such that the gas supply unit supplies the purge gas to the filter at a preset flow rate. The gas supply unit is in particular dimensioned such that by means of it flow rates between 0.1 l/min and 20 l/min can be realized so that a correspondingly large range of transfer capacities is possible and thus the amount of carbon dioxide to be removed can be adapted to the condition of the patient as exactly as possible.

In a particularly preferred embodiment, the control unit comprises an input and/or output unit for the output of information to an operator and/or for the input of information by the operator. The output information in particular comprises the carbon dioxide contents of the purge gas determined by means of the sensors and/or the determined flow rates so that the operator can easily monitor whether the planned amount of carbon dioxide has been removed from the flow of blood. The input information preferably comprises control data by means of which the operator can control the arrangement. In particular, the operator can set the desired flow rate of the purge gas and/or the composition of the purge gas via the input unit and can thus also ensure how much carbon dioxide is removed from the extracorporeal flow of blood. The input and output unit is in particular designed as a touchscreen so that only one single unit is required for input and output, and this single unit can be operated by the operator easily and intuitively. Thus, input errors are avoided and a simple handling is achieved.

A further aspect of the invention relates to a method for removing carbon dioxide from an extracorporeal flow of blood in which a flow of blood is passed through a blood region of a filter separated from a gas region by a membrane and in which a gas flow of a purge gas is passed through the gas region. As a purge gas, an inert gas or a mixture of inert gases is used, in particular nitrogen or a noble gas being used as an inert gas or a mixture of nitrogen and at least one noble gas or a mixture of at least two noble gases being used as a mixture.

BRIEF DESCRIPTION OF THE DRAWINGS

Further features and advantages of the invention result from the following description which explains the invention on the basis of embodiments in connection with the attached Figures, in which.

DETAILED DESCRIPTION

Figure 1:
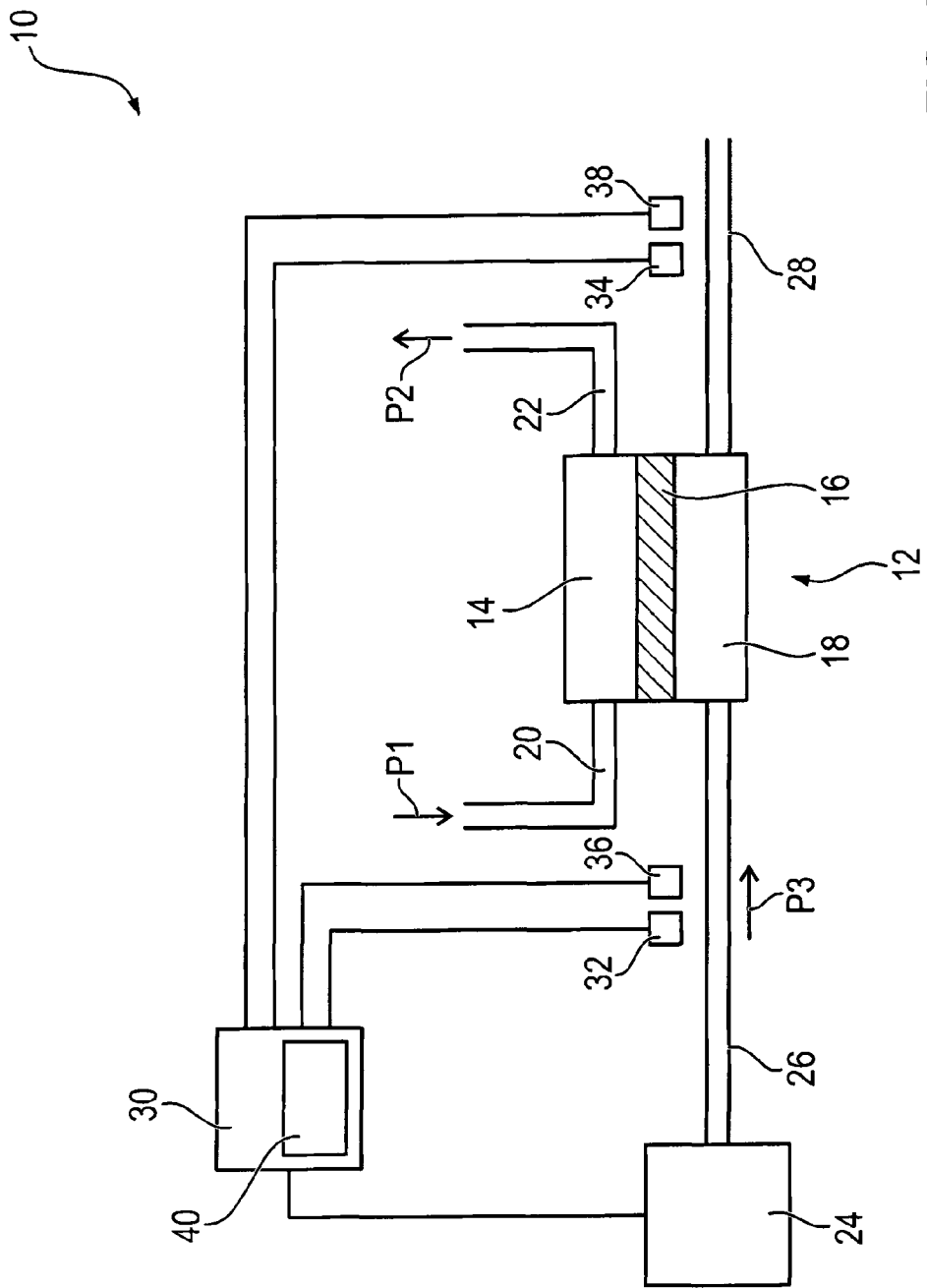
FIG. 1 shows a schematic illustration of an arrangement for removing carbon dioxide from an extracorporeal flow of blood according to a first embodiment.

In FIG. 1, a schematic illustration of an arrangement 10 for removing carbon dioxide from an extracorporeal flow of blood of a patient is illustrated. The arrangement 10 comprises a filter designed as an oxygenator 12 and having a blood region 14 and a gas region 18 separated from this blood region 14 via a membrane 16. The extracorporeal flow of blood is passed through the blood region 14 according to the arrows P1 and P2, for which a supply line 20 and a discharge line 22 are provided.

A purge gas contained in a storage tank 24 and supplied to the gas region 18 via a supply line 26 is passed through the gas region 18, which is indicated by the arrow P3.

According to the invention, an inert gas or a mixture of inert gases is used as a purge gas, wherein each gas that does not enter into combination with blood can be used as an inert gas. As a result of the pressure difference of the partial pressure of the carbon dioxide between the blood region 14 and the gas region 18 or the concentration difference between the blood region 14 and the gas region 18, carbon dioxide is removed from the flow of blood through the membrane 16 and is supplied to the purge gas so that the carbon dioxide content of the flow of blood is reduced. Since the inert gas used as a purge gas or the mixture of inert gases used as a purge gas cannot itself enter into combination with the blood, no enrichment of the flow of blood with the inert gas takes place. As the inert gas in particular does not comprise any oxygen, merely a removal of the carbon dioxide from the flow of blood but no oxygenation of the flow of blood takes place by the oxygenator 12. Thus, the patient, from which the flow of blood is taken, is not irritated by the enrichment with oxygen so that in particular a hypoxic pulmonary vasoconstriction with a corresponding shunt shift is prevented. Hereby, also other negative influences on the blood-gas-related supply condition of the already critically ill patient are prevented. Shunt shift in this connection means that the limit up to which the fine blood vessels of the lung are supplied with blood changes.

As an inert gas, in particular nitrogen or a noble gas or a mixture of the afore-mentioned gases is used. As a noble gas, in particular helium, neon, argon, krypton or xenon is used.

The purge gas enriched with the carbon dioxide is discharged via the discharge line 28 and is, for example, supplied to a recycling system.

Further, the arrangement 10 comprises a control unit 30, two carbon dioxide sensors 32, 34 for determining the carbon dioxide content of the purge gas and two flow rate sensors 36, 38 for determining the flow rate of the purge gas. One carbon dioxide sensor 32, 34 and one flow rate sensor 36, 38 each are arranged upstream of the oxygenator 12 and downstream of the oxygenator 12.

The control unit 30 has a touchscreen 40 by means of which information can be output to an operator of the arrangement 10 and information, in particular data for controlling the arrangement 10, such as a desired amount of carbon dioxide to be removed from the extracorporeal blood flow, can be input. The values determined by means of the sensors 32 to 38 are in particular displayed to the operator via the touchscreen 40 so that the operator can easily monitor the planned function of the arrangement 10. In particular, the control unit 30 determines a difference value from the value determined by means of the carbon dioxide sensor 34 and the value determined by means of the carbon dioxide sensor 32 so that via a—in particular graphic—display of this difference value the operator can easily see how much carbon dioxide has been removed from the flow of blood.

Further, the operator can set the flow rate at which the purge gas is to flow through the gas region 18 via the control unit 30 so that via the flow rate the transfer capacity of the carbon dioxide, i.e. the amount of carbon dioxide which is removed from the flow of blood can easily be controlled. The flow rate is in particular settable in a range between 0.1 l/min and 20 l/min. For this, the control unit 30 controls the storage tank 24, in particular a valve of the storage tank 24 such that this storage tank supplies a purge gas flow at a corresponding flow rate into the supply line 26 and thus to the gas region 18.

In a preferred embodiment, a closed-loop control system is formed by the flow rate sensor 36 and/or the flow rate sensor 38. In this case, the control unit 30 compares the actual value of the flow rate of the purge gas determined by the flow rate sensor 36 and/or by the flow rate sensor 38 to a preset desired value of the flow rate and controls the storage tank 34 such that the actual value corresponds to the desired value.

In an alternative embodiment, it is likewise possible that the flow of the purge gas is not exclusively generated via the pressure with which the purge gas is contained in the storage tank 24, but a further separate gas supply unit for generating the flow of purge gas through the gas region 18 is provided.

Figure 2:
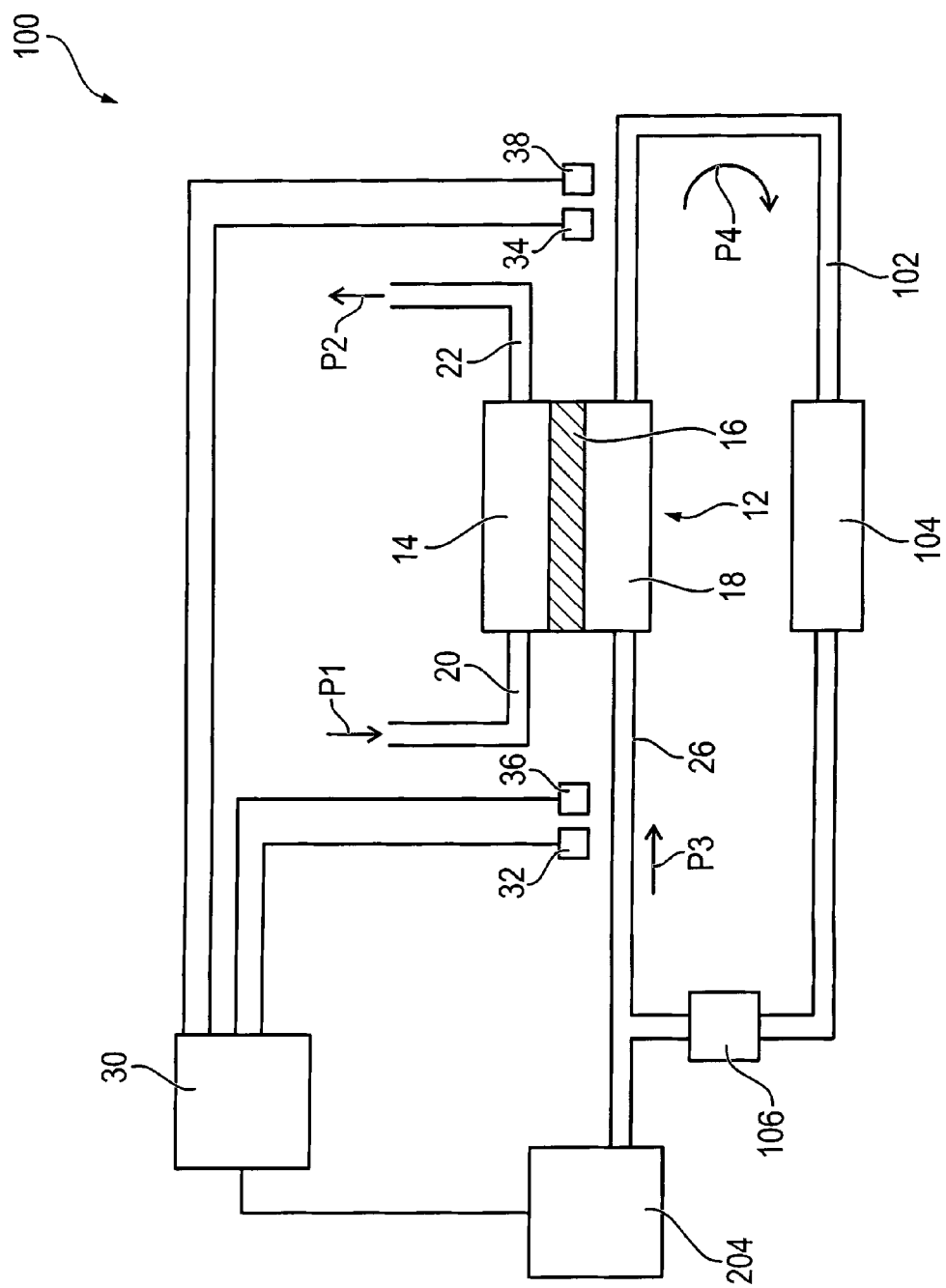
FIG. 2 shows a schematic illustration of an arrangement for removing carbon dioxide from an extracorporeal flow of blood according to a second embodiment.

In FIG. 2, a schematic illustration of an arrangement 100 for removing carbon dioxide from an extracorporeal flow of blood according to a second embodiment is illustrated. The second embodiment differs from the first embodiment shown in FIG. 1 in that the purge gas is not disposed after passage through the gas region 18, but is supplied to the supply line 26 via a return line 102, as indicated by the arrow P4, so that the purge gas can be used several times. Thus, it is not necessary to always take "fresh" purge gas from the storage tank 24 and to supply it to the gas region 18.

In the area of the return line 102, a cleaning unit 104 for removing carbon dioxide from the purge gas returned by the return line is provided. This cleaning unit 104 is in particular designed such that by means of this cleaning unit the carbon dioxide can be completely removed from the purge gas so that only pure purge gas without carbon dioxide is supplied to the supply line 26. Alternatively, only a part of the carbon dioxide can be removed as well. The cleaning unit 104 is in particular designed such that therein in the purge gas being passed through the carbon dioxide contained in the purge gas is bound and thus removed from the purge gas by chemical processes such as under adsorption through a container with soda or soda line or equipped with a further permeable membrane.

Further, in the return line 102 a ventilator 106 is arranged, by which the gas flow of the purge gas is maintained.

Figure 3:
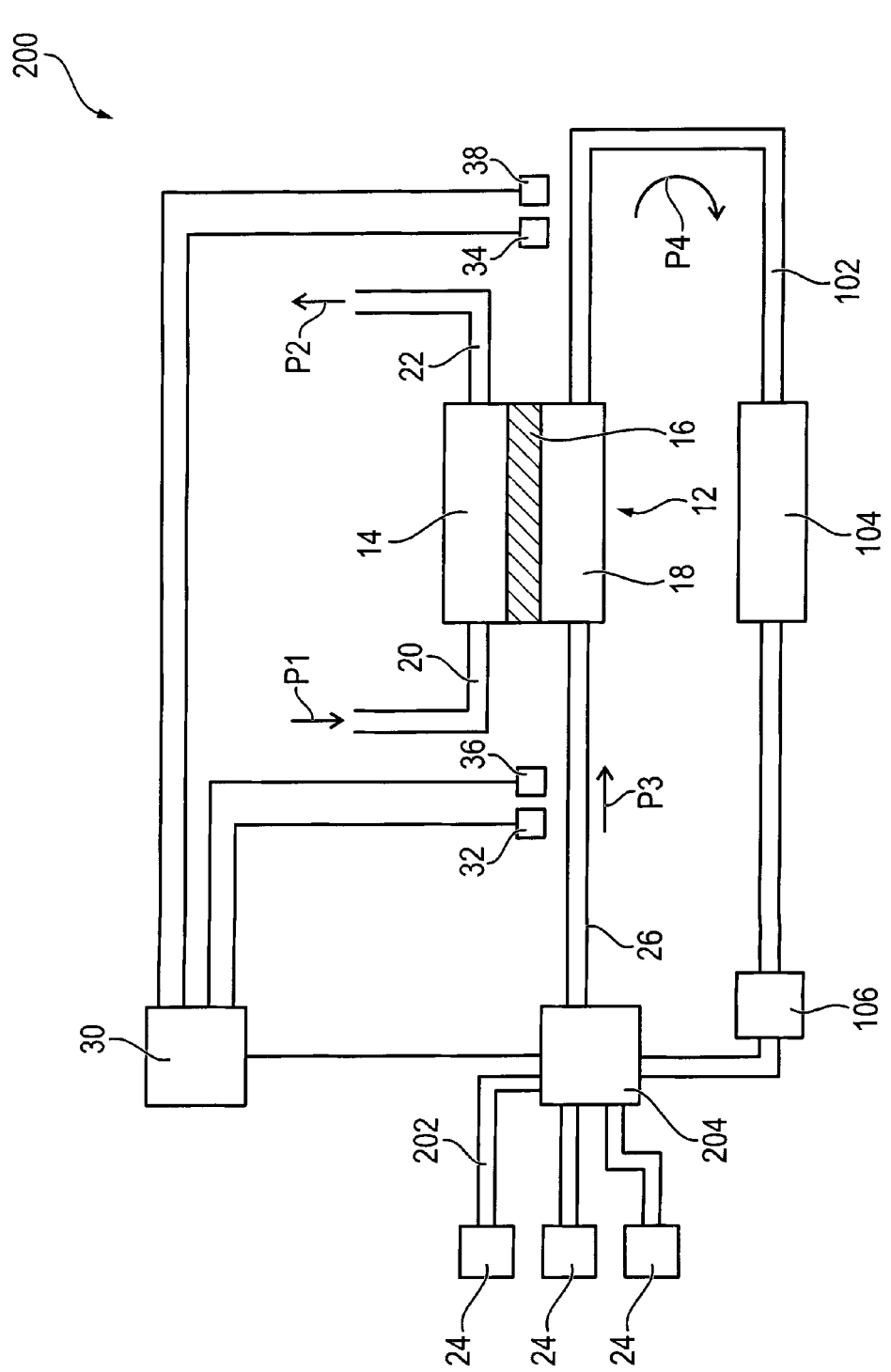
FIG. 3 shows a schematic illustration of an arrangement for removing carbon dioxide from an extracorporeal flow of blood according to a third embodiment.

In FIG. 3, a schematic illustration of an arrangement 200 for removing carbon dioxide from an extracorporeal flow of blood according to a third embodiment is illustrated. In contrast to the first two embodiments, the arrangement 200, in this third embodiment, has not only one storage tank 24 filled with a gas, but three storage tanks 24 each filled with gas. The storage tanks 24 are each connected via a line 202 to a gas mixing unit 204 which is also referred to as a gas blender so that via the gas mixing unit 204 the purge gas that is thereafter fed from the gas blender 204 to the oxygenator 12 is mixed from the gases contained in the storage tanks 24. In the storage tanks 24 in particular one inert gas each is contained so that via the gas mixing unit 204 a mixture of these inert gases can be mixed as a purge gas. Alternatively, in one or more storage tanks 24 a mixture of inert gases can already be contained.

Via the gas mixing unit 204 also only one of the gases contained in the storage tanks 24 can be supplied to the supply line 26 so that in this case merely this one gas serves as a purge gas. Thus, the gas mixing unit 204 can serve, on the one hand, to mix a purge gas from several gases and, on the other hand, also to allow for an option of the purge gas without the storage tank 24 having to be changed for this.

The return line 102 is in particular also connected to the gas mixing unit 204 so that the returned purge gas can be mixed via the gas mixing unit 204 with gases that are possibly taken from the storage tanks 24. Alternatively, the connection of the return line 102 to the supply line 26 can also be realized downstream of the gas mixing unit 204.

Further, it is alternatively possible that more than three storage tanks 24, for example four storage tanks 24, or also only two storage tanks 24 are provided.

Further, it is alternatively possible that only in some of the storage tanks 24 inert gases and in the other storage tanks 24 no inert gases, for example oxygen or an oxygen-nitrogen-mixture, is contained. Hereby, it is achieved that patients from which not only carbon dioxide is to be removed from the flow of blood but the flow of blood also has to be enriched with oxygen, for example because the own breathing capacity of the patient is not sufficient therefor, this can take place via the same arrangement 200.

The composition of the purge gas from the gases contained in the storage tanks 24 can in particular be set via the control unit 30. Thus, the composition of the purge gas can easily be adapted to the respective patient-dependent circumstances.

In a further alternative embodiment of the invention, as in the third embodiment, also several storage tanks 24 can be provided, from which gases the purge gas can be mixed by means of a gas mixing unit 204 and, on the other hand however, as in the first embodiment according to FIG. 1, no return of the purge gas after passage through the oxygenator 12 takes place. In this case, the purge gas is disposed and/or recycled after passing through the oxygenator 12.

Although various embodiments of the present invention have been described and shown, the invention is not restricted thereto, but may also be embodied in other ways within the scope of the subject-matter defined in the following claims.

What is claimed is:

1. An arrangement for removing carbon dioxide from an extracorporeal flow of blood, comprising:

a filter comprising a membrane that separates a blood region through which the extracorporeal flow of blood is passed from a gas region through which a flow of a purge gas is passed;

a cleaning unit that removes carbon dioxide from the flow of the purge gas passed through the gas region of the filter; and both downstream and upstream of the filter one carbon dioxide sensor is provided for each location for determining the carbon dioxide content of the purge gas, and each carbon dioxide sensor is operably connected to a control unit so that carbon dioxide content values determined by the carbon dioxide sensors are displayed via a touchscreen of the control unit, wherein the purge gas does not include oxygen and is an inert gas selected from the group consisting of nitrogen, helium, neon, argon, xenon and krypton; or the purge gas does not include oxygen and is a mixture of two or more gases selected from the group consisting of nitrogen, helium, neon, argon, xenon and krypton.

2. The arrangement according to claim 1, wherein the arrangement comprises a gas supply unit for generating the gas flow of the purge gas or a blood pump for transporting the flow of blood through the blood region.

3. The arrangement according to claim 2, wherein the gas supply unit comprises a gas mixing unit or a ventilator.

4. The arrangement according to claim 1, wherein at least one purge gas storage tank is provided in which the purge gas is contained, and in that the purge gas storage tank is connected to the filter via a supply line.

5. The arrangement according to claim 4, wherein a return line for returning the purge gas from the filter into the supply line is provided.

6. The arrangement according to claim 5, wherein the cleaning unit for removing carbon dioxide is arranged in the area of the return line.

7. The arrangement according to claim 1, wherein downstream or upstream of the filter one sensor each for determining the flow rate of the purge gas is provided.

8. The arrangement according to claim 1, wherein the control unit controls the flow of gas such that the purge gas is supplied to the filter at a preset flow rate between 0.1 l/min and 20 l/min.

9. The arrangement according to claim 8, wherein the touchscreen is operable for the output of information to an operator or for the input of control data by an operator.

* * * * *